(12) United States Patent
Habib

(10) Patent No.: US 8,357,153 B2
(45) Date of Patent: Jan. 22, 2013

(54) APPARATUS FOR ADMINISTERING THERAPY AT A REMOTE LOCATION IN THE BODY

(75) Inventor: Nagy Habib, London (GB)

(73) Assignee: Emcision Ltd., London (GB)

( * ) Notice: Subject to any disclaimer, the term of this patent is extended or adjusted under 35 U.S.C. 154(b) by 662 days.

(21) Appl. No.: 12/522,721

(22) PCT Filed: Jan. 11, 2008

(86) PCT No.: PCT/GB2008/000084
§ 371 (c)(1),
(2), (4) Date: Dec. 9, 2009

(87) PCT Pub. No.: WO2008/084239
PCT Pub. Date: Jul. 17, 2008

(65) Prior Publication Data
US 2010/0106149 A1    Apr. 29, 2010

(30) Foreign Application Priority Data

Jan. 11, 2007   (GB) .................................. 0700553.1
Apr. 13, 2007   (GB) .................................. 0707370.3
Dec. 13, 2007   (GB) .................................. 0724347.0

(51) Int. Cl.
*A61B 18/14* (2006.01)
(52) U.S. Cl. ..................... 606/41; 607/101; 607/116
(58) Field of Classification Search ............ 606/41, 606/45–50; 607/101, 102, 115, 116
See application file for complete search history.

(56) References Cited

U.S. PATENT DOCUMENTS

| | | | | |
|---|---|---|---|---|
| 5,122,136 A | * | 6/1992 | Guglielmi et al. | 606/32 |
| 5,234,437 A | * | 8/1993 | Sepetka | 606/108 |
| 5,250,071 A | * | 10/1993 | Palermo | 606/198 |
| 5,281,217 A | * | 1/1994 | Edwards et al. | 606/41 |
| 5,709,224 A | * | 1/1998 | Behl et al. | 128/898 |
| 5,851,206 A | * | 12/1998 | Guglielmi et al. | 606/28 |
| 5,972,026 A | * | 10/1999 | Laufer et al. | 607/96 |
| 6,179,832 B1 | * | 1/2001 | Jones et al. | 606/32 |
| 6,190,353 B1 | | 2/2001 | Makower et al. | |

(Continued)

FOREIGN PATENT DOCUMENTS

WO   94/03213 A   2/1994

(Continued)

OTHER PUBLICATIONS

International Search Report for International Application No. PCT/GB2008/000084.

*Primary Examiner* — Michael Peffley
(74) *Attorney, Agent, or Firm* — Caesar, Rivise, Bernstein, Cohen & Pokotilow, Ltd.

(57) ABSTRACT

Devices suitable for insertion into a hollow anatomical structure within a patient for the purpose of ablating tissue within or surrounding the hollow structure so as to induce occlusion of the hollow structure are provided. The devices are in the form of guidewires with functional tips, that comprise at least one heating module, at their distal ends. The devices of the invention are suitable for occluding hollow anatomical structures selected from vasculature or from non-vascular ducts and tubes, via percutaneous, laparoscopic or endoscopic routes of access. Methods of using the devices in the treatment of patients are also described.

3 Claims, 16 Drawing Sheets

U.S. PATENT DOCUMENTS

| | | | |
|---|---|---|---|
| 6,726,677 B1 | 4/2004 | Flaherty et al. | |
| 6,979,330 B2 * | 12/2005 | Kelly et al. | 606/41 |
| 7,674,262 B2 * | 3/2010 | Sugita et al. | 606/45 |
| 2002/0151886 A1 | 10/2002 | Wood | |
| 2004/0181215 A1 | 9/2004 | Kelly et al. | |
| 2005/0043727 A1 | 2/2005 | Swanson et al. | |

FOREIGN PATENT DOCUMENTS

| | | |
|---|---|---|
| WO | 99/56812 A | 11/1999 |
| WO | 00/72909 A | 12/2000 |
| WO | 02/32333 A | 4/2002 |
| WO | 2006/062873 A | 6/2006 |

* cited by examiner

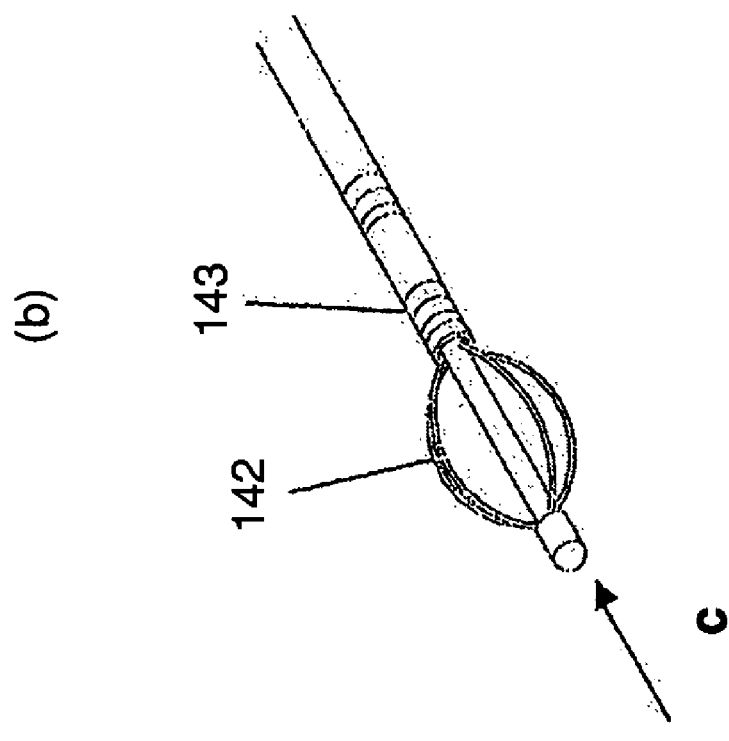
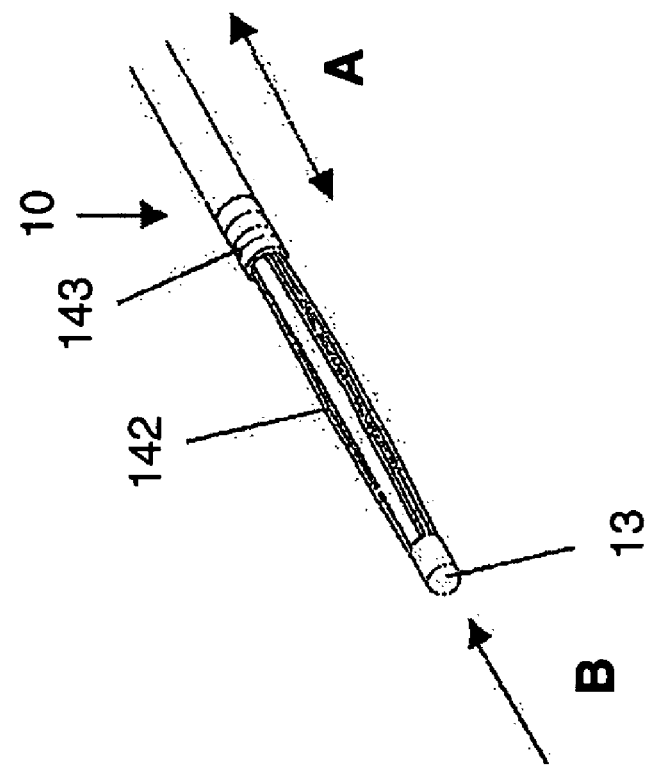
FIGURE 4

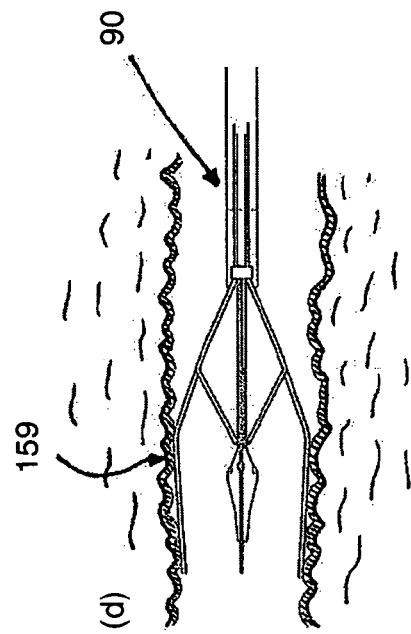
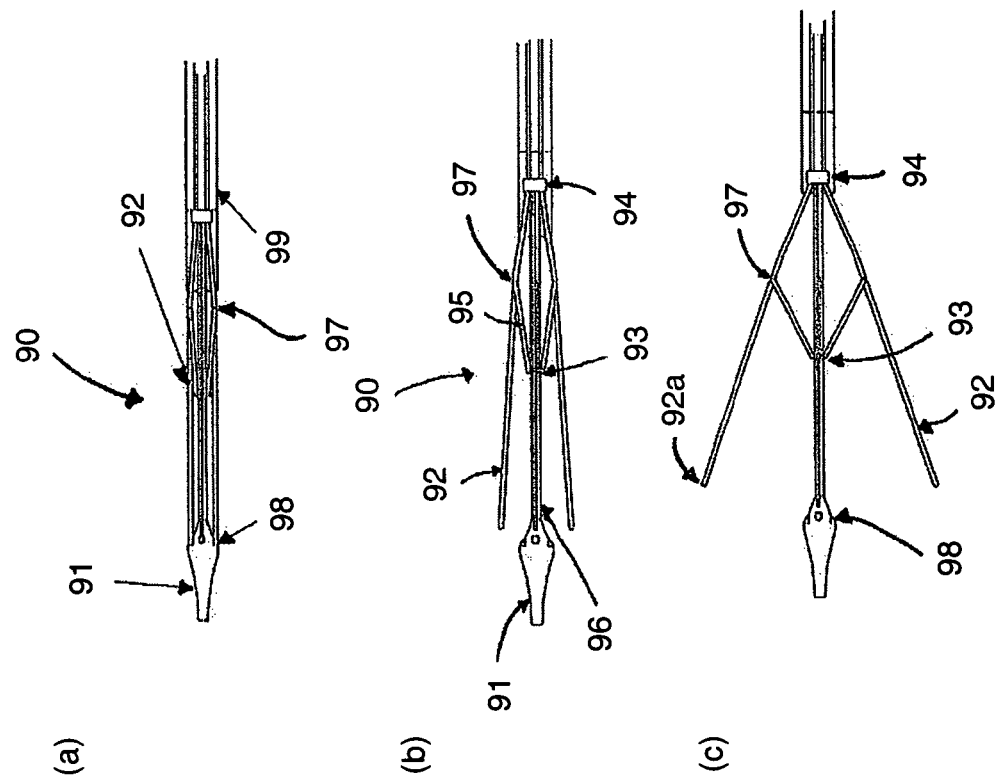
FIGURE 6

FIGURE 7
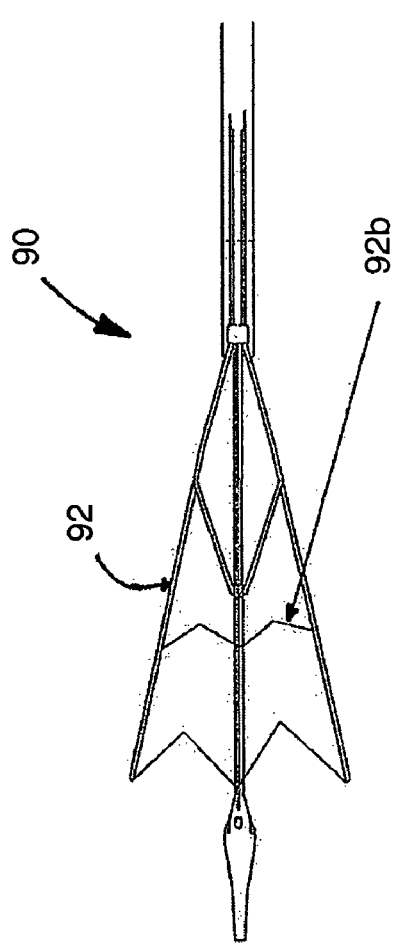
(a)
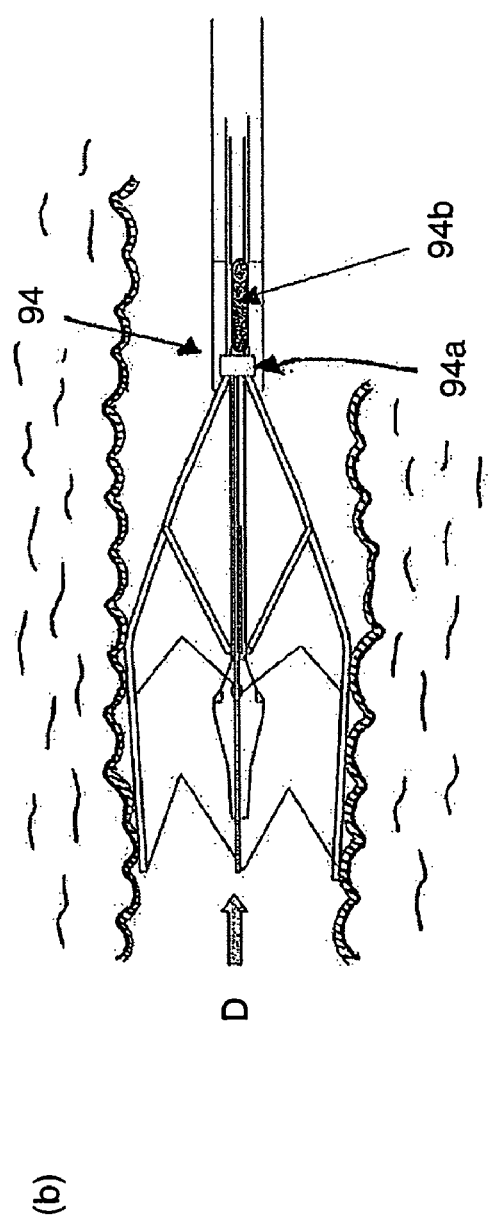
(b)

(d)

APPARATUS FOR ADMINISTERING THERAPY AT A REMOTE LOCATION IN THE BODY

CROSS-REFERENCE TO RELATED APPLICATIONS

This national stage application claims the benefit under 35 U.S.C. §371 of International Application No. PCT/GB2008/000084 filed on Jan. 11, 2008, entitled APPARATUS FOR ADMINISTERING THERAPY AT A REMOTE LOCATION IN THE BODY, which in turn takes its priority from Great Britain Application No. 0700553.1 filed on Jan. 11, 2007, Great Britain Application No. 0707370.3 filed on Apr. 13, 2007, and Great Britain Application No. 0724347.0 filed on Dec. 13, 2007, and all of whose entire disclosures are incorporated by reference herein.

BACKGROUND OF THE INVENTION

1. Field of Invention

The invention relates to apparatus and methods for performing endoscopic, laparoscopic and percutaneous interventional surgery.

2. Description of Related Art

This invention is in the surgical therapies for the treatment of disease by blocking, or occluding, hollow anatomical structures within the body of a patient. The invention also relates to surgical therapies for the treatment of the surface of a hollow anatomical structure, wherein such treatments do not necessarily result in occlusion of the structure.

In many medical conditions such as arterio-venous vascular malformations and varicose veins, it is advantageous to block a blood vessel. In treating liver disease it is possible to induce liver regeneration by directing blood supply from one area to another, for example by blockage of portal blood to the right liver to induce hypertrophy of the left liver. Blocking blood flow can also be used in the field of oncology, specifically in the field of treating solid tumours. One method of treating tumours is to interrupt the blood supply to the tumour. In many tumours there are a small number of discrete vessels supplying blood to the tumour. Interrupting the blood supply to these vessels will cease the flow of nutrients to the tumour causing the tumour cells to die. Blood vessels that supply tumours can also be used to introduce an ablation device into the tumour.

Occlusion of non-blood vessels can also be desirable. Hollow anatomical structures include, for example, the fallopian tubes, small and large intestine, bronchi, bronchioles, biliary duct, urethra, ureters and vas deferens. In certain circumstances it may be desirable to occlude (fully or partially) a hollow anatomical structure. For example; ligation of the fallopian tubes is a well known means for achieving female sterilization. In other circumstances it may be desirable to treat the lumen-facing surface of the hollow structure so as to administer therapy to a lesion that is located on that surface.

Prior methods of inducing closure or occlusion of a hollow anatomical structure include injecting a sealing compound into the structure, or positioning a plug or obstructive stent into the structure. These have the disadvantage that these blocking structures may move over time. For instance, where a blood vessel that leads to a tumour has been occluded loss or displacement of the occluding structure can permit resumption of blood flow through the tumour supplying vessel. In some cases the structure may move to another vessel and cause an embolism.

Thermal ablation of hollow anatomical structures has been utilised in the percutaneous treatment of venous disorders such as varicose veins as well as in endoscopic tubal ligation for achieving female sterilization. Hollow anatomical structures, such as blood vessels, are treated in this way by local heating. This heating may be applied by exposing the tissue in the tube or vessel to locally applied electro-magnetic or ultrasound energy. The electro-magnetic energy may be at radio-frequencies, or micro-wave radiation. The effect of the heating on the treated tissue is two-fold. First, hollow structures will be sealed, and permanent occlusion of the structure achieved. Second, the surrounding tissue that is heated will be coagulated, causing cell death and shrinkage.

Conventional methods for administering thermal ablation to hollow anatomical structures, such as the vasculature or various ducts in the body, are typically based on the use of one or more therapeutic catheters that are slidably mounted over a prepositioned guidewire. The disadvantage of this system is that the arrangement sets functional limitations upon the minimum lumen diameter of the anatomical structure that can be treated due to the combined diameter of guidewire and catheter. Hence, for oncology, paediatric/neonatal, neurovascular, cerebrovascular or cardiovascular applications, where the lumen diameters can be very small, such percutaneous or endoscopic thermal ablation techniques can be unsuitable.

Hence there is a need for improved apparatus and methods for managing occlusion of hollow anatomical structures and thermally ablating tissues. In particular, there is a need for methods and apparatus that can be directed to blockage of blood vessels at remote sites within the body that are inaccessible to conventional surgical techniques, such as the brain and the smaller vessels of the heart. There is further need for methods and apparatus for occluding or treating hollow anatomical structures within the body that are not comprised within the vasculature via endoscopic or laparoscopic routes.

BRIEF SUMMARY OF THE INVENTION

In its primary aspect the invention provides a device suitable for insertion into a hollow anatomical structure within a patient for the purpose of ablating tissue within or surrounding the hollow structure so as to induce occlusion of the hollow structure, the device comprising:

a body having a distal end and a proximal end, the body comprising a central core which extends along the length of the body, the central core comprising a plurality of steering members and at least one conductor, the at least one conductor having a connection to an external energy source; and a tip located at the distal end of the body, wherein the tip comprises a heating module, and wherein the heating module is in contact with the at least one conductor;

wherein, in use, when the tip is located within the hollow structure the external energy source is activated, thereby inducing activation of the heating module and facilitating ablation of said structure and/or the surrounding tissue.

Typically the heating module comprises at least one electrode that is capable of expansion outwardly from the tip so as to achieve improved physical contact with the walls of the surrounding hollow anatomical structure. The body, suitably, has mean diameter along its length of between about 0.1 mm and about 3 mm, and as such the body may be in the form of what is conventionally termed a 'guidewire'.

Optionally, the device comprises means for permitting in situ detachment of the tip following activation of the ablating module. Further, the device can suitably comprise a plurality of sequentially detachable tips located at the distal end of the body.

The means for connecting the at least one conductor to an external energy source may suitably comprise a housing that is slidably mounted on the body, the housing including an actuator means for controlling electrical contact between the at least one conductor and the external energy source. Optionally, the external energy source is an RF generator.

A further aspect of the invention provides a guidewire device suitable for insertion into a hollow anatomical structure within a patient via a percutaneous, laparoscopic or endoscopic route for the purpose of ablating tissue within or surrounding the hollow structure so as to induce occlusion of the hollow structure, the device comprising:

- a body having a distal end and a proximal end, the body comprising a central core which extends along the length of the body, the central core comprising a plurality of steering members and at least one conductor, the at least one conductor having a connection to an external energy source; and
- a tip located at the distal end of the body, wherein the tip comprises at least one expandable heating module capable of heating the walls of the hollow structure to a temperature that causes endoluminal closure of the hollow structure, and wherein the heating module is in contact with the at least one conductor;

wherein, in use, when the tip is located within the hollow structure the heating module is expanded so as to contact the surface of the hollow structure, and the external energy source is activated, thereby causing endoluminal closure of the hollow structure.

A further aspect of the invention provides for a device suitable for insertion into a hollow anatomical structure within a patient via a percutaneous, laparoscopic or endoscopic route for the purpose of ablating tissue within or surrounding the hollow structure so as to induce occlusion of the hollow structure, the device comprising:

- a guidewire having a distal end and a proximal end, the guidewire comprising a central core which extends along the length of the body, the central core comprising at least one conductor and a plurality of steering members, a tip located at the distal end of the guidewire wherein the tip comprises a heating module and means for connecting the at least one conductor to an external energy source, said means being located at the proximal end of the guidewire; and
- a catheter having a elongate body including a lumen extending along at least a portion of the elongate body, wherein the lumen is adapted to facilitate slidable mounting of the catheter on the guidewire, an aperture positioned in the side wall of the catheter proximally to the distal end of the catheter, the aperture being sealable via a pivotally mounted door;

wherein, in use, the guidewire can be withdrawn proximally until the distal tip of the guidewire is located within the lumen of the catheter at a point that is adjacent to the aperture which permits the door to be opened inwardly, such that upon subsequent advancement of the guidewire the tip is deflected outwardly from the lumen of the catheter through the aperture and into the surrounding hollow anatomical structure where the heating module can be activated so as to induce ablation of the tissue.

In specific embodiments the devices of the invention are suitable for transluminal use in hollow anatomical structures including but not limited a vein: an artery; an arteriole; a fallopian tube; a biliary duct; a ureter; a urethra; a bronchiole; and a vas deferens. The invention is also suitably used for administering treatment to ducts, vessels or tubes within the body that can be accessed endoscopically, laparscopically or percutaneously.

In an aspect of the invention there is provided a method of treating a patient requiring endoluminal closure of a hollow anatomical structure, comprising locating a device as described herein within a hollow anatomical structure within the body of the patient, ablating tissue within or surrounding the hollow structure so as to induce occlusion of the hollow structure and withdrawing the device from the body of the patient. In one embodiment of the invention the patient is suffering from cancer and the hollow structure is located adjacent to or within a solid tumour. In a specific embodiment of the invention the hollow structure is a fallopian tube and the patient requires tubal ligation. In a further specific embodiment of the invention the hollow anatomical structure is a blood vessel (e.g. vein, artery, or arteriole) located within the cerebrovasculature, typically the brain, of the patient.

BRIEF DESCRIPTION OF SEVERAL VIEWS OF THE DRAWINGS

FIG. 6 shows a side view of the distal tip of an alternate embodiment of the guidewire of the invention in which the guidewire includes an expandable electrode structure that is shown in the process of deploying in (a) to (c). (d) shows the expanded structure within a hollow anatomical structure, demonstrating the increased contact between the flexible electrode arms and the walls of the hollow structure.

FIG. 7 shows a side view of the distal tip of the embodiment of the guidewire of the invention as shown in FIG. 6, (a) displays the further inclusion of additional radial electrode wires that retractably extend across the span between the expanded flexible electrode arms thereby providing additional contact area with the surface of the surrounding hollow structure walls. (b) shows an additional embodiment of the invention in which a resilient member is located at the proximal end of the expandable structure and allows for a controlled level of movement of the hub, thereby improving the ability to maintain contact between the pliable electrode arms and the walls during movement of the guidewire within the hollow anatomical structure.

DETAILED DESCRIPTION OF THE INVENTION

In the embodiments described herein the term 'guidewire' is used to describe the elongate filament-like device of the invention which is utilised to administer therapy within the body via a percutaneous surgical technique. The devices of the invention are typically of composite manufacture and comprise thermal ablation functionality at or near their distal tips. Hence, the devices of the invention are described as 'guidewires' largely because of their resemblance to conventional wires that are used to guide catheters slidably mounted thereon, and because they can continue to function as conventional guidewires if the need arises. However, it is envisaged that for many embodiments the devices described according to the present invention are stand-alone devices that do not rely on a separate catheter for functionality.

Figure 1:
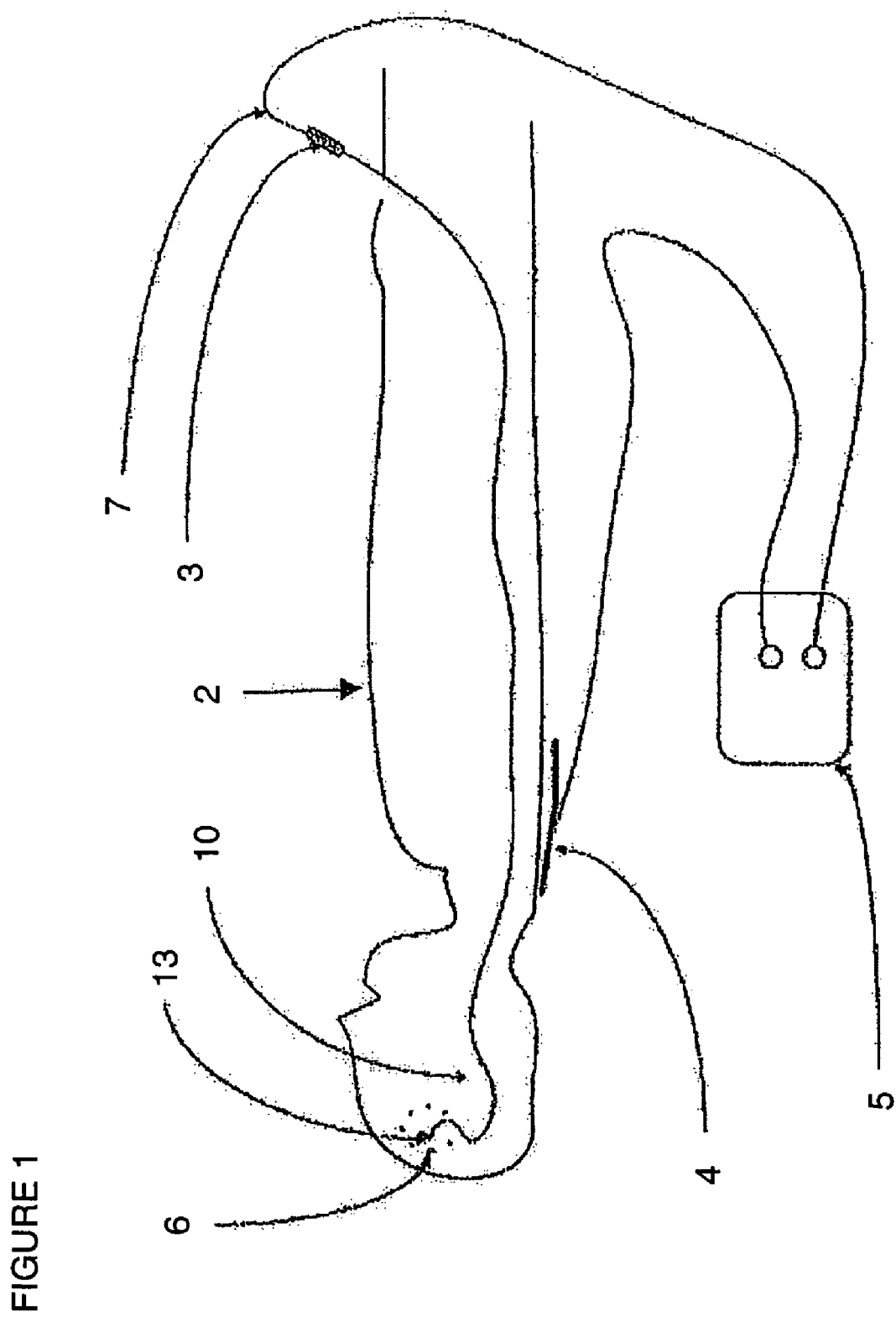
FIG. 1 shows a diagrammatic view of an embodiment of a guidewire of the invention in use in a patient.

FIG. 1 shows a typical embodiment of a device of the present invention where a lesion 6 such as a tumour or haemorrhage is located at an inoperable site in the body of a patient 2 and requires treatment. A guidewire 10 is inserted via a percutaneous route, such as a femoral artery access, and tracked up the vascular system to the tumour site 6. In the present instance the target site may be in the brain or another part of the body. The guidewire 10 has a distal tip 13 which may comprise, or be located adjacent to, an electrode 14 (see FIG. 2). The distal tip 13 may also comprise a radio-opaque material to facilitate navigation of the device to the tumour site 6. The guidewire is conducting and can conduct an applied RF signal from a connector 3 at the proximal end to the distal tip 13. The proximal connector mates with a matching connector on a lead 7 that is connected to one polarity of an RF generator 5. The other polarity of the RF generator is connected to a electrode pad 4 that is placed in contact with the patient's body 2.

In RF configuration the electrode 14 located at the distal tip 13 comprises a single electrode and so it is said that the that the RF is applied in monopolar mode. The RF current is preferably at a frequency between 100 kHz and 5 MHz. The device can be used in two different modes. The device can be inserted into one or more blood vessels that provide a blood supply to a solid tumour, so the distal end is positioned at any point in the vessel close to but upstream to the tumour (i.e. in an artery or arteriole). RF energy is then applied causing heating of the surrounding tissue, including collagen and other extracellular matrix components in the vessel wall, which causes the vessel to collapse and prevent blood flow into the tumour. In another mode the device can be inserted into a vessel in the centre of the tumour and the RF energy is applied to also heat the surrounding tissue beyond the vessel wall. This embodiment of the invention is particularly suitable where the surrounding tissue is a tumour. Alternative arrangements are possible when other energy sources are used such as microwave or ultrasound. Likewise, alternative embodiments include use of the device in non-vascular hollow anatomical structures.

Typically the guidewires of the invention are operated according to three main phases of therapy: an insertion phase, a therapy phase and a removal phase. The insertion phase includes the percutaneous insertion of the guidewire and the location of the guidewire to the site where therapy is to be administered. The therapy phase includes the steps of deploying the electrode and administering thermal ablation to the walls of the hollow anatomical structure, and optionally the surrounding tissue. The removal phase includes the withdrawal of the guidewire from the site of ablation, usually back along the initial insertion path. Optionally, the therapy phase and withdrawal phase can overlap such that ablation is applied along a portion of the hollow anatomical structure rather than simply at a single site.

Figure 2:
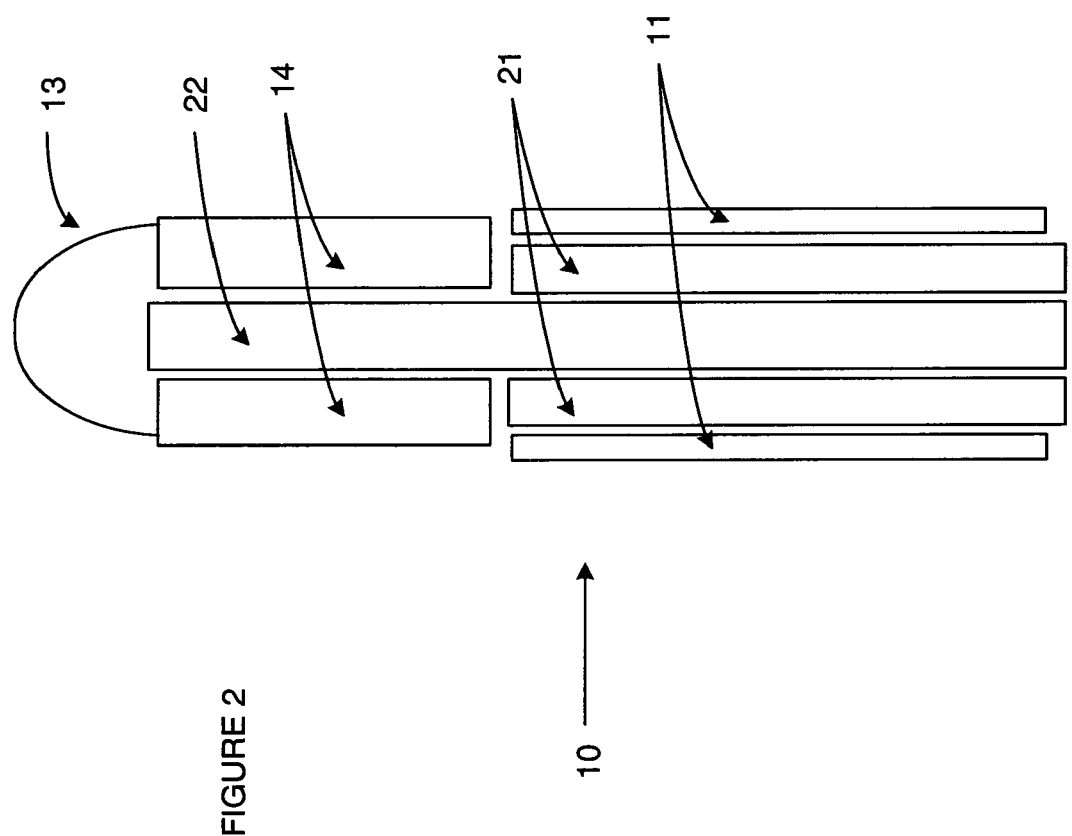
FIG. 2 shows a cut away side view of the distal end tip of a guidewire of the invention demonstrating the location of the electrode tip.
Figure 8:
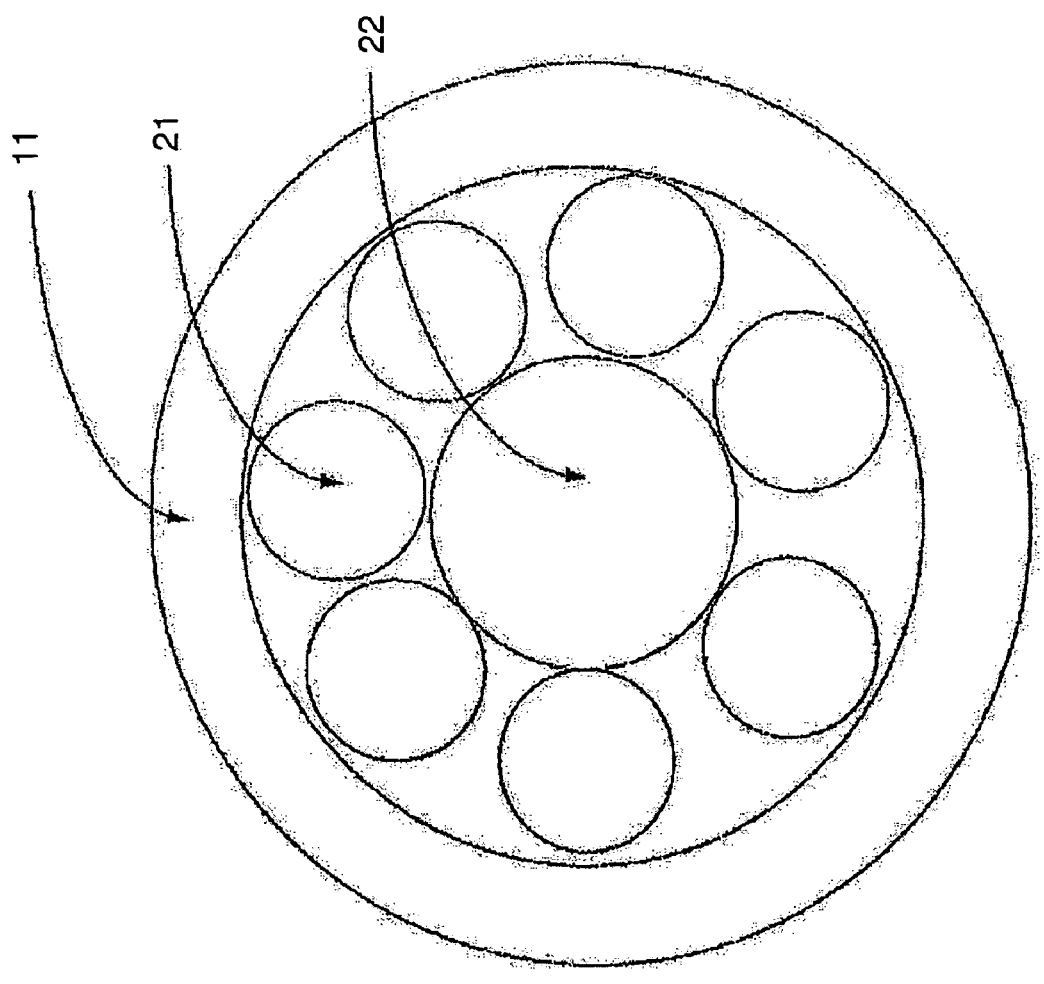
FIG. 8 shows a schematic cross sectional view of an embodiment of the guidewire of the invention showing an arrangement of six steering wires surrounding a central conductor core, the arrangement is enclosed within an outer insulating coating.

FIG. 2 shows details of the construction of the distal region of the guidewire 10. The guidewire 10 suitably possesses a number of properties relating to electrical conductivity, flexibility, steerability and pushability. For this combination a composite construction is desirable, as one single material component typically cannot simultaneously provide the required electrical conductivity, and required steerability. A conducting core 22, suitably constructed from a high conductivity material, such as copper, silver or gold wire, provides the conductivity, and a plurality of steering members 21, suitably steel or nitinol wires, provide the mechanical properties including pushability. The steering members 21 can be arrayed about the central conducting core 22 as shown in FIG. 8. In embodiments of the invention the central core is enclosed with an insulating material, such as a polyimide sheath. An insulating coating 11 made from a low friction material such as a fluoropolymer (e.g. PTFE) suitably covers and encapsulates the assembly, to provide a low-friction surface and electrical insulation. The coating 11 typically stops short of the distal tip 13 to allow the electrode 14 to be exposed to the surrounding tissue when in use. The outer diameter of the guidewire assembly is typically in the range of about 0.1 mm to about 3 mm (about 0.005 inches to about 0.14 inches). Where a monopolar RF configuration is desired the guidewire device of the invention comprises a single central conducting core 22. In embodiments of the invention where a bipolar RF configuration is desired (i.e. wherein the guidewire distal tip 13 comprises two electrodes of opposing polarity) the central core 22 will contain two conductor wires (one for each polarity) each enclosed within a separate insulating sheath.

Figure 3:
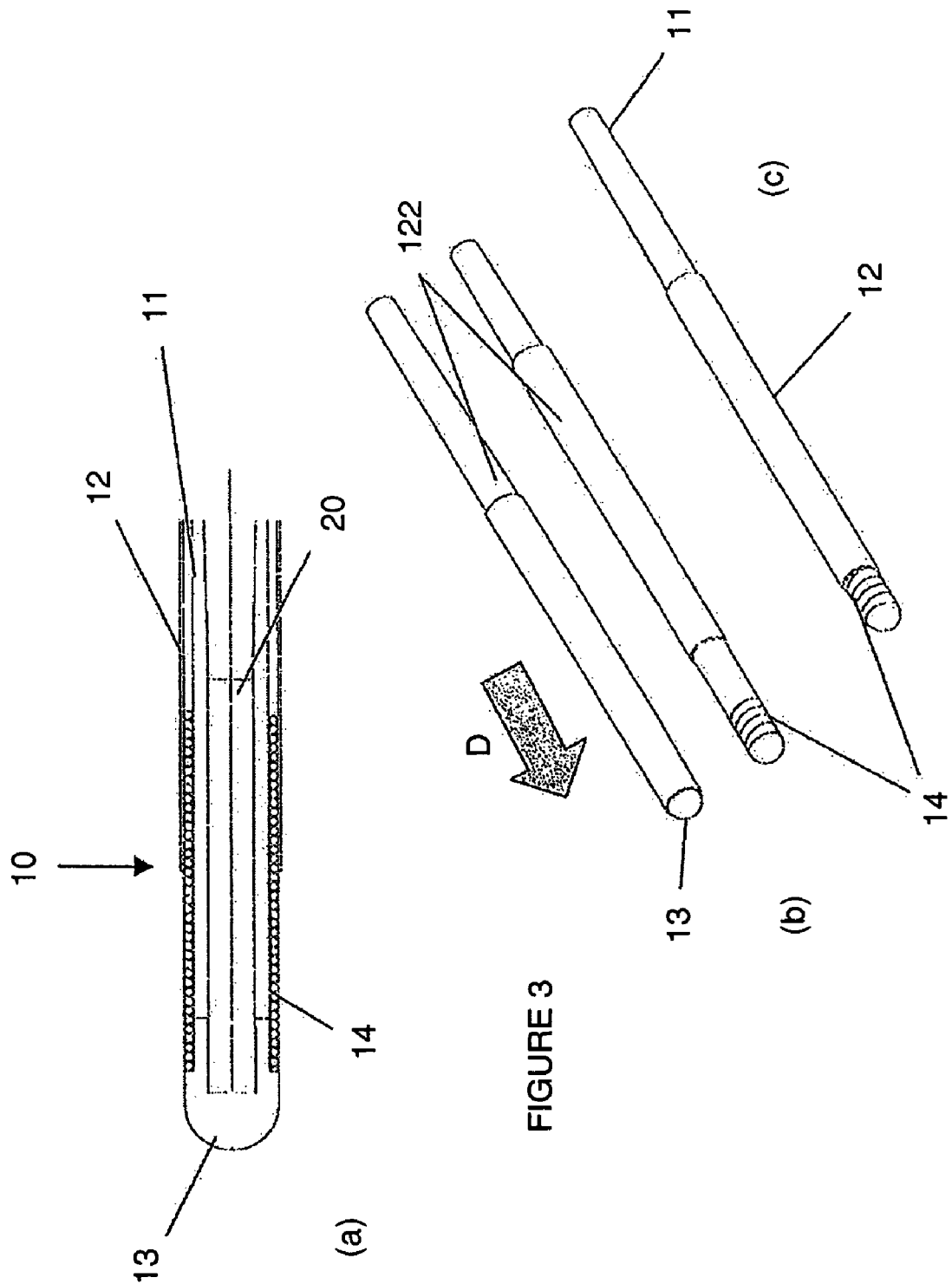
FIG. 3 shows two embodiments of the distal end tip of FIG. 2, (a) shows a cut away side view of the distal end tip which also includes a outer sleeve, (b) shows an oblique view of an embodiment where the outer sleeve is adjustable and can be retracted to expose or shroud the electrode tip, sliding movement is along the longitudinal axis of the guidewire as denoted by arrow D; (c) shows an embodiment where the sleeve is static.

FIG. 3 shows details of the tip. The core 20 comprises the conducting core 22 and the steering members 21 and is positioned at the centre of the assembly and lies along the whole length of the guidewire 10, thereby defining the longitudinal axis of the device. The coating 11, and the steering members 21 terminate a short distance from the distal tip 13. The remaining length will have a series of short conducting wires connecting to the conductor 22. These wires act as the outer contact surface of the tip, forming an electrode 14, and enable electrical contact to be made with the surrounding tissues. A smooth, conical or hemi-spherical cap may be attached to the tip 13 of the assembly to ease insertion into the hollow anatomical structure. In a specific embodiment of the invention an outer sheath 12 is retractably located in the distal region of the guidewire 10 (see FIG. 3 (b)) allowing the amount of electrode 14 exposed to the surrounding tissue to be adjusted. Alternatively, the sheath 12 can be static and serves as an additional layer of insulation in the tip region (see FIG. 3 (c)).

Figure 4:
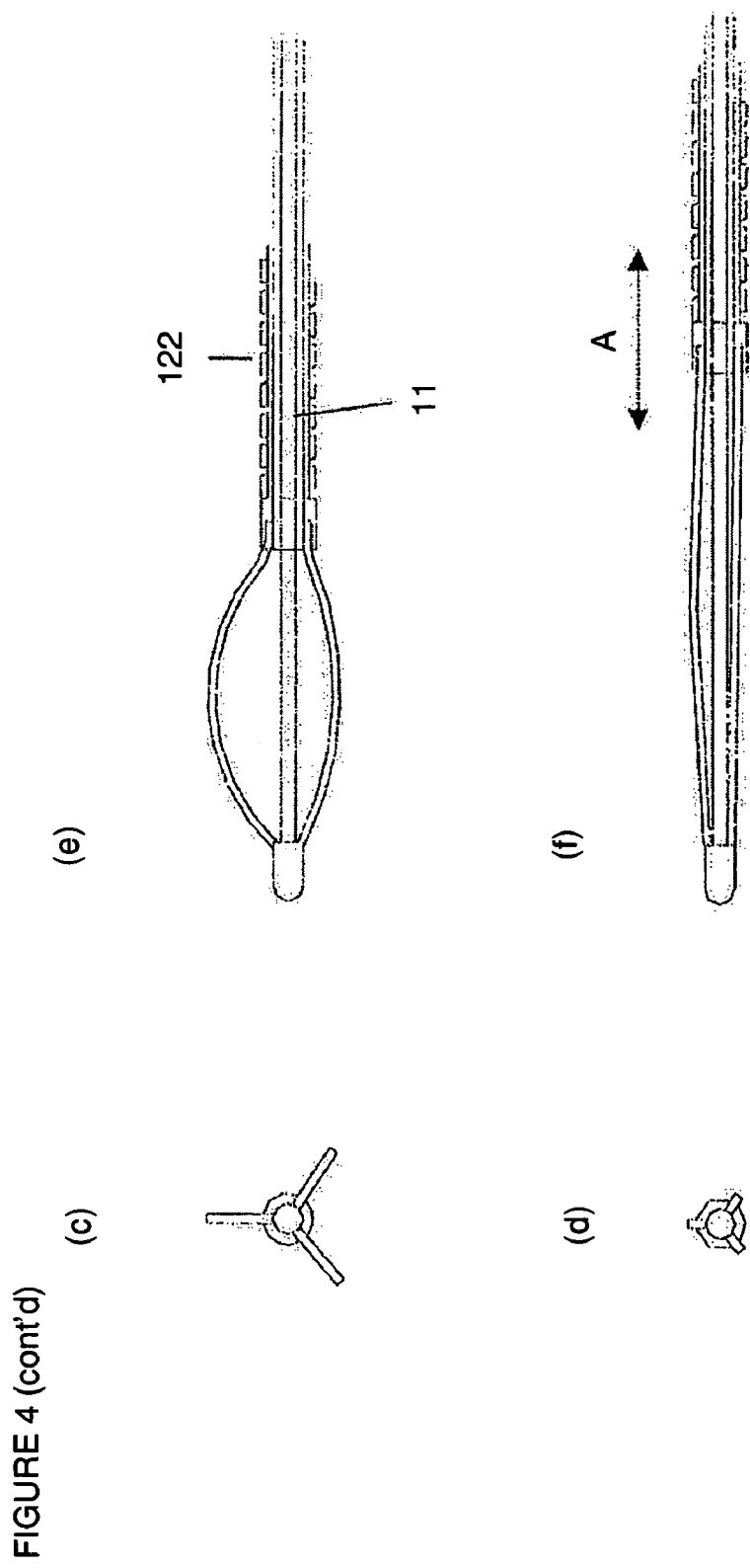
FIG. 4 (a) shows an oblique view of the distal tip of an embodiment of the guidewire of the invention which comprises an expandable spring electrode in the undeployed state. (b) shows the spring electrode in the deployed or expanded state. (c) Shows an axial view along line C in FIG. 4 (b). (d) shows an axial view along line B in FIG. 4 (a). (e) shows a side view of the guidewire with the spring electrode in the expanded state, in an additional embodiment a helical outer sleeve is provided that surrounds the exterior surface of the guidewire. (f) shows a side view of the guidewire with the spring electrode in the unexpanded state.

The configuration of the electrode 14, represents a particular embodiment of the present invention. In FIG. 4 one configuration of the guidewire electrode 142 is shown which comprises an expandable structure both allowing for improved contact between the surface of the electrode and walls of the surrounding structure as well as anchoring the guidewire in its location. FIG. 4 (a) shows a guidewire electrode 142 comprising an expandable basket arrangement, referred to as a spring electrode that includes deformable splines secured at either end to a static tip 13 and a slidable collar 143. When deployment of the electrode is required the collar 143 is able to be moved slidably in the direction shown by arrow A in order to reduce the longitudinal distance between the collar 143 and the tip 13 causing the deformable splines of the electrode 142 to bow radially outward, as shown in FIG. 4 (b). Views along the longitudinal axis of the guidewire are shown in FIGS. 4 (c-d) further showing the radial expansion of the spring electrode 142. In a specific embodiment of the invention an additional spring sheath 122 in the form of a spiralled shaft is applied to at least a portion of the exterior of the insulating coating 11 at the location of the collar 143, which accommodates the need for expansion of the insulation when the collar 143 is slid towards the tip 13 (see FIGS. 4 (e-f)). The expanded spring electrode is retracted following administration of therapy by initiating sliding of the collar 143 in the reverse direction to that to arrow A (FIG. 4 (a)).

Figure 5:
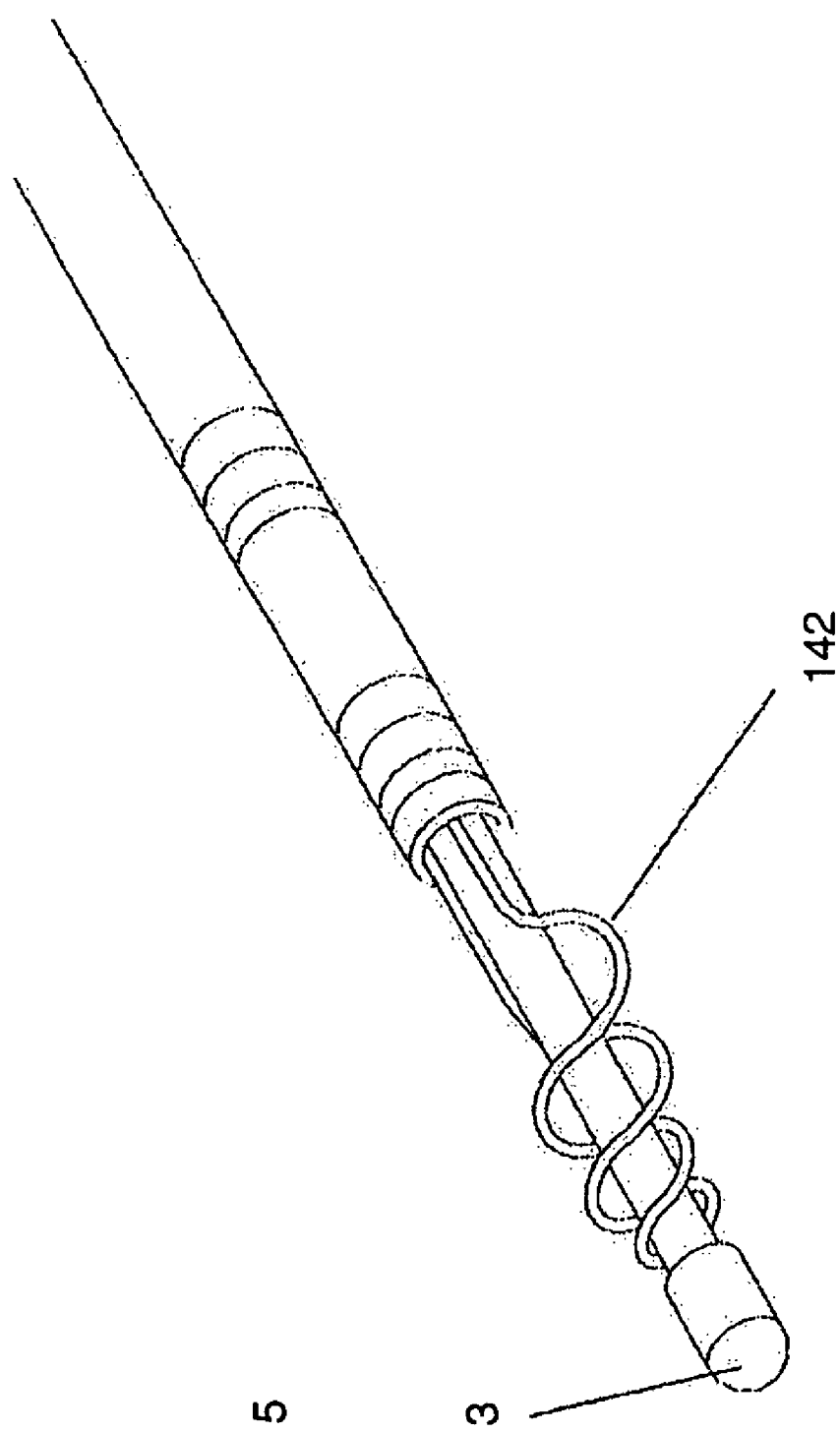
FIG. 5 shows an oblique view of the distal tip of an alternate embodiment of the guidewire of the invention in which the guidewire further comprises an expandable structure that takes the form of a bipolar double helix coil spring electrode.

The expandable electrode 142 need not be limited to the configuration described above and shown in FIG. 4. In FIG. 5 an alternative arrangement is shown in which the expandable structure is in the form of a helical or coil spring. Operation of the expansion/retraction of the electrode is substantially similar to that described previously. However, one advantage of the helical coil spring configuration is that it is possible to provide a bipolar RF electrode configuration solely on the guidewire by adopting a double helical structure wherein each strand of the helix provides the opposite polarity. In this embodiment, a separate electrode pad 4 is not required. Such an arrangement may be suitable in hollow anatomical structures (e.g. blood vessels) that are particularly small, for instance, where the diameter of the lumen is less than 2 mm, or even less than 1 mm.

A further embodiment of the invention includes an alternative conformation for an expandable electrode located on the distal tip of the guidewire. FIG. 6 (a-c) shows an expandable 'umbrella' electrode configuration. The guidewire 90 is provided with a tip 91 located at the distal (i.e. forward) end of a central flexible shaft 96. An annular collar 93 is slidably mounted on the shaft 96 proximally (i.e. to the rear) of the tip 91. A statically mounted hub 94 is located at a position proximally to the collar 93. Elongated flexible electrode arms 92 have an end pivotally anchored to the hub 94 and a free end 92a that extends in a distal direction. Each electrode arm 92 is either fixedly or pivotally connected to the first end of a strut 95 at an interim location 97 on the arm 92 between the hub 94 anchor point and the free end 92a. The second end of the strut 95 is pivotally anchored to the collar 93. In use, the guidewire 90 is inserted into the hollow anatomical structure and directed to the site where therapy is to be directed. During the insertion phase the umbrella electrode is kept in a retracted state with the electrode arms 92 held parallel to the longitudinal axis of the shaft 96, this being achieved by maximising the distance between the slidable collar 93 and the hub 94. In this configuration the free ends 92a of the arms 92 are housed within notches 98 formed in the proximally facing portion of the tip 91. When expansion of the electrode arms 92 is required, the collar 93 is drawn towards the hub 94 reducing the distance there-between and enabling the struts 95 to bear on the arms 92 causing the free ends 92a to extend outwardly from guidewire 90 towards the surrounding walls 159 (see FIG. 6(d)). In this manner the expansion of the electrode broadly mimics the opening of an umbrella.

As with the other embodiments of the invention flexible electrode arms 92 are suitably manufactured from a resilient and conductive material, for instance, stainless steel or a shape memory alloy such as nitinol. The pliability of the arms 92 is advantageous as it allows for improved contact with the walls 159 of the hollow anatomical structure and which can match the sometimes-complex surface topography over an extended area. This is particularly of advantage, for example, if the electrode is expanded for use within a varicose vein or within a tortuous oviduct.

The pivotal connections between the electrode arm 92 and the hub 94, the strut 95 and the collar 93, and optionally the strut 95 and the arm 92, can suitably be in the form of an articulated joint or hinge. In a further embodiment of the invention a resilient member 94b can be located proximal to semi-fixed hub 94a (see FIG. 7(b)), this allows for the hub 94a to be displaced proximally by a certain amount in response to compression exerted on the flexible arms 92 by the contracting vessel walls during the thermal ablation step. By allowing a certain amount of free longitudinal movement of the hub 94 the contact between the arms 92 and the walls of the hollow anatomical structure can be maintained, particularly if the expanded electrode is in the process of being withdrawn from the from the hollow anatomical structure whilst the ablation is occurring (as indicated by directional arrow D in FIG. 7(b)). The resilient member 94b is suitably tensioned to provide an appropriate biasing force against the hub 94a. The resilient member 94b may comprise a resilient or elastic polymeric material or a spring.

Contact between the expanded umbrella electrode and the walls can be increased by inclusion of additional electrode cross wires 92b that extend across the span between adjacent expanded flexible electrode arms 92 so as to be arrayed circumferentially about the longitudinal axis of the shaft 96 (see FIG. 7 (a)). The combination of the flexible arms 92 together with the spanning cross wires 92b effectively converts the expandable electrode into an expandable web-like structure. The additional cross wires 92b are suitably manufactured from similar materials to those used to make the flexible arms 92. It should be noted that the inclusion of additional cross wires is not limited to the expandable umbrella electrode embodiment of the invention, but can also extend to the other expandable electrode configurations described above.

In a specific embodiment of the invention it is desirable to provide a device comprising a detachable distal end tip, which end tip comprises the electrode. Typically, the end tip will be detached following the therapy phase after thermal ablation of the hollow anatomical structure has occurred. This may be necessary in situations where there is tissue adhesion to the electrode surface as a result of heating and there exists a risk of haemorrhage or damage to peripheral healthy tissue if the electrode were to be withdrawn. In such an embodiment of the invention, one or more detachment mechanisms can be employed that facilitate release of the distal end tip and, thus, removal of the guidewire device following the therapy phase. The detached end tip remains in the body of the patient following treatment and can serve as an additional occluding structure to assist in maintenance of the integrity of the occlusion.

Figure 9:
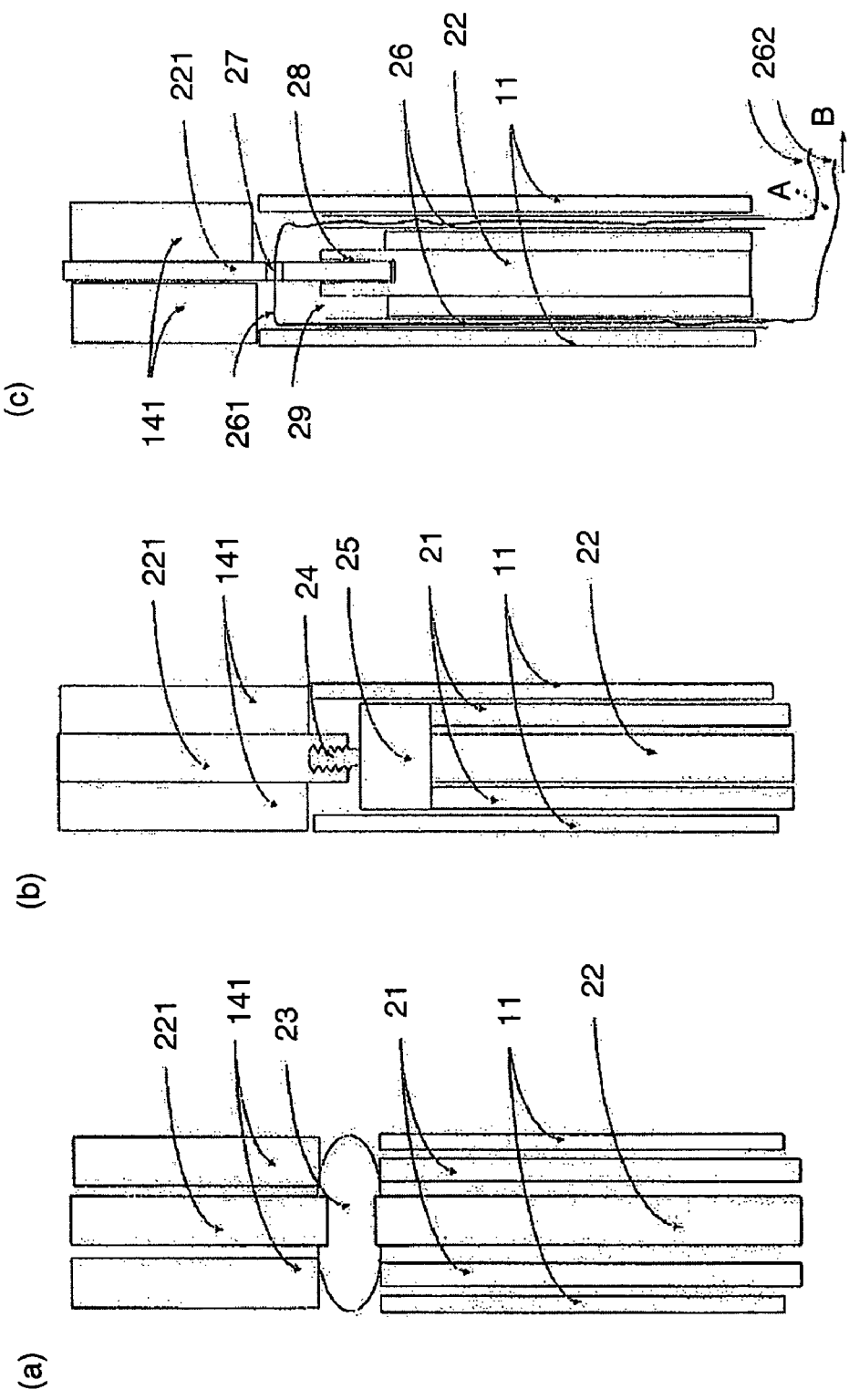
FIG. 9 shows cut away side views of the distal tip of embodiments of the invention in which the distal tip is detachable from the body of the guidewire in use, (a) shows an embodiment wherein the distal tip is joined to the body via a weld of joining material, (b) shows an embodiment where the joining is mediated via a threaded, joint and where a threaded connecting post is retractable into the body of the guidewire thereby releasing the tip from the guidewire body, (c) shows an embodiment where the detachable tip engages with the body of the guidewire via a post and socket arrangement and is secured via a removable tether that passes through an aperture formed in the post, (d) shows an embodiment where the distal tip is joined to the body of the guidewire via a magnetic linkage, (e) shows an embodiment in which the distal tip is linked to the body of the guidewire via a releasable latching mechanism, (f) shows a similar embodiment to (e) but wherein the latching arms are released from engagement with the distal tip by retraction of the adjustable outer coating which can be slidably displaced along the axis shown by line y.
Figure 9:
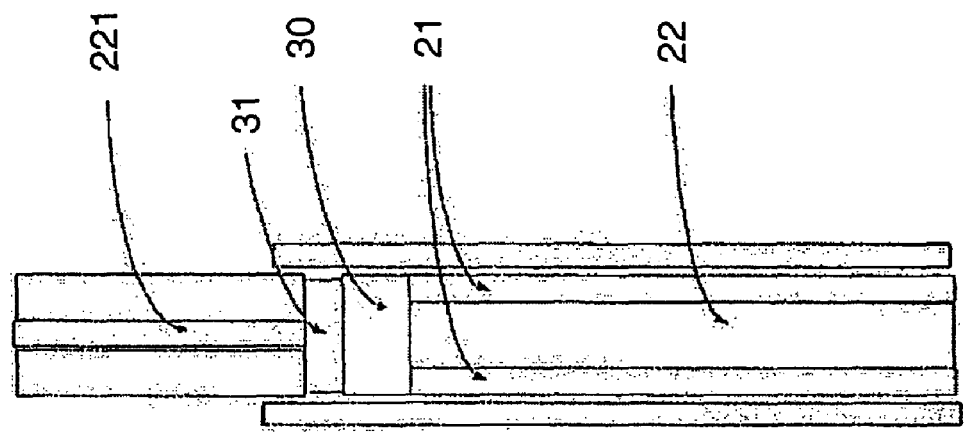
Figure 9:
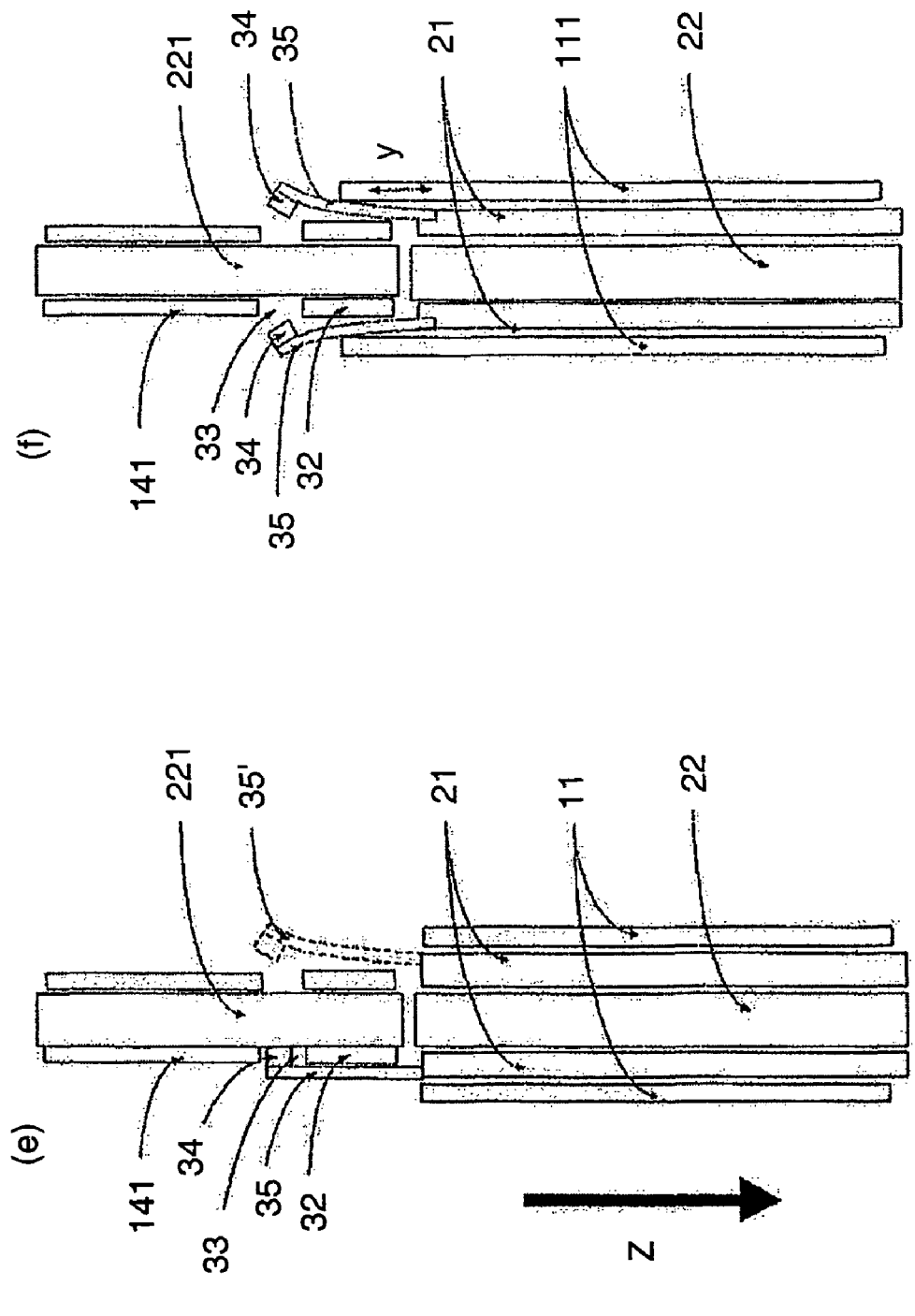

A number of suitable detachment mechanisms are provided by the invention for facilitating the release of the distal end tip in situ following the therapy phase and are shown in FIG. 9 (a-f). It should be noted that the detachment mechanisms described are suitable for use with any or all of the aforementioned expandable electrode configurations.

FIG. 9 (a) shows an embodiment comprising a detachable tip. A central conductor core 221 is affixed to the central conductor 22 of the guidewire 10 with a disc of joining material 23. Electrode contacts 141 are attached to the central conductor core 221 and provide an ablation surface that contacts the surrounding tissue when in use. The joining material 23 comprises a material that will dissolve or melt during or shortly after thermal ablation, permitting the tip assembly to detach. In one embodiment the material is made of a suitable electrolytically erodeable metal, such as stainless steel. The electrode contacts 141 are suitably made of a material which is less electrolytically erodeable, such as platinum. In use, when a DC current is passed from the distal tip to a nearby electrode such as the patient electrode pad 4 or a needle inserted into nearby tissue, the joining material 23 will be eroded by electrolytic action. When the joining disc is eroded sufficiently, the tip will detach, allowing the main guidewire body 10 to be withdrawn. In another embodiment of the invention the joining material 23 comprises a material with a low melting point, such as wax, or polypropylene. When the tissue surrounding the tip is heated by the application of RF energy, the temperature of this joining disc will be raised to a value when the material of the disc beings to soften, and no longer joins the tip to the main guidewire body.

Another embodiment of the invention comprising a detachable tip is shown in FIG. 9 (b), in which the terminus of the main guidewire body 10 comprises is a retaining member 25 that includes a threaded joining member 24. The joining member 24 is able to engage with a matching threaded cavity formed in the proximally facing portion of the central conducting core 221 in the distal tip. The distal tip is detached from the guidewire body 10 by rotating the main guidewire about its longitudinal axis body so as to unscrew the guide wire body 10 from the distal tip. It will be appreciated that the distal tip will be anchored into the tissue following the thermal ablation due to adhesion between the ablated tissue and the electrode contacts 221.

FIG. 9 (c) shows a further embodiment of the invention comprising a detachable tip. The central conductor core 22 of the main guidewire body 10 comprises a socket 28 formed in the distally facing terminus of the core 22. The central conductor core 221 of the distal tip is of a dimension that allows it to be received within the socket so as to enable a male/female engagement. The engagement is secured via a tether 261, suitably a wire, fine cable or thread (e.g. nylon thread), which passes along the length of the guidewire body 10 via channels 26 located adjacent to the steering members 21, and passes through an aperture 27 formed in the central conductor core 221. Typically the tether channels 26 will be defined by an insulated conduit that allows free movement of the tether along the channel. In use, the tether forms a loop through the aperture 27 and anchors the detachable tip to the body of the guidewire 10. the ends of the tether 262 exit from the proximal end of the guidewire outside of the patients body 2. To detach the distal tip the tether can simply be withdrawn from the device by pulling on one of the ends 262 in direction B. Alternatively, the tether can be cut at position A, and one of the ends 262, is pulled to remove the loop of wire from the guidewire 10, again in direction B.

A further embodiment of the detachable tip is shown in FIG. 9 (d) in which a magnetic release mechanism utilised. The central conductor core 22 of the main guidewire body 10 is attached to a permanent magnet 30. The magnet suitably comprises a material based on Neodynium-Boron, or a similar high coercivity and high remanence material. The material is modified to have a Curie temperature in the range of the thermal ablation temperature. The central conductor core 221 of the detachable distal tip is attached to a ferromagnetic yoke 31 located at the proximally facing side of the detachable distal tip. In use, the yoke 31 engages the magnet 30 via magnetic attraction. During thermal ablation, the distal tip region is heated to the ablation temperature, at which point the magnet 30 loses its magnetic properties, and the tip becomes detached from the guidewire body 10, thereby permitting removal of the guidewire device.

Another embodiment of the detachable tip assembly is shown in FIG. 9 (e). extending distally from the distal terminus of the steering members 21 of the main guidewire body 10 are two or more deformable latching arms 35. At the distal end of each arm 35 there is located a locking member 34, suitably a lug, which is capable of engaging with a recess 33 formed in the surface of the distal end tip. The recess 33 may be in the form of a depression, or as a groove that extends around the circumference of the distal end tip and which is defined by a space between the proximal end portion of the electrode contacts 141 and an annular retaining ring 32. In use, when the arms 35 are in the extended positions and the locking members 34 engaged with the recess 33, the distal tip is secured to the main guidewire body 10. The arms 35 are suitably made of a material that changes shape with temperature. The arms 35 may comprise a bimetallic strip, made of a laminate of two materials of different thermal expansion coefficients such as bronze and steel. Alternatively the arms 35 can comprise nitinol used in shape memory mode, with the transition temperature suitably arranged to coincide with the thermal ablation temperature. When the distal tip is heated, during the therapy phase, the arms 35 will deform outwardly (as shown by deformed arm 35') so that the locking member 34 no longer engages with the recess 33. When the arms 35' are deformed the distal tip is no longer anchored to the guidewire body 10 and can be can detached. Although the figures show the deformable latching arms 35 as separate components from the steering members 21, in an embodiment of the invention the arms 35 are simply integral distal extensions of the steering members.

A similar embodiment to that described above is shown in FIG. 9 (f). Located at the distal terminus of the steering members 21 of the main guidewire body 10 are two or more deformable latching arms 35 in a configuration akin to that described previously. The deformable arms comprise an elastic material which is configured such that so that the arms 35 are splayed outwardly when unconstrained so that the locking members 34 are disengaged from the recess 33. The elastic material may suitably comprise spring steel, or nitinol in super-elastic mode. A slideable mounted sleeve 111 enshrouds at least the distal portion of the guidewire body 10 and is capable of reciprocal movement along the longitudinal axis of the device as shown by arrow y. When the sleeve 111 is moved distally the arms 35 will be urged into a configuration that is parallel to the guidewire axis, so that the locking members 34 engage with the recess 33 and the distal tip is attached to the guidewire body. When the sleeve 111 is moved proximally, the arms 35 will splay outwardly and the locking members 34 disengage from the recess 33 and the distal tip will detach from the main guidewire body 10.

In both the embodiments described above, the latching arms 35 can serve to provide an electrical connection between the core conductor 22 of the guidewire body 10 and the central core 221 of the distal tip.

In specific embodiments of the invention, the device may contain more than one detachable distal tips. For example, a plurality of detachable tips can be 'stacked' at the distal end region of the device and sequentially released either in a single location or at multiple discrete locations within the patient's body. In this way, the invention permits use of the device in a single-entry-multiple-treatment format. This arrangement is particularly suited to clinical indications where several lesions, tumours or metastases are present within or proximate to the hollow anatomical structure and all require ablation during a single surgical procedure. One or more of the above described tip detachment mechanisms can be combined into a single device if necessary in embodiments of the invention relating to the multiple detachable tip arrangement.

By way of example, methods of the invention using the device comprising a detachable tip can typically include the following steps.

i) Insertion of the guidewire device into the patient through a suitable endoscopic, laparoscopic or vascular access port.
ii) Manoeuvre of the guidewire so that the distal tip is located in an appropriate hollow anatomical structure, this may be a blood vessel supplying a lesion, inside the lesion, inside an arterio-venous malformation or within a tube or duct.
iii) Connection of the proximal end of the guidewire assembly to a radiofrequency (RF) generator.
iv) Application of RF power to the electrode tip via the central conductor core, using a patient electrode pad as the return electrode (monopolar configuration).
v) Cessation of application of power when the hollow anatomical structure is sealed or the surrounding tissue is ablated.
vi) If not already achieved during (v), activation of the tip detachment mechanism, and separation of the distal tip from the main body of the guidewire.
vii) Withdrawal of the main body of the guidewire device from the patient.

In embodiments of the invention where multiple detachable distal tips are used, steps (ii) to (vi) are repeated as necessary prior to withdrawal of the device from the patient's body.

Whilst devices of the invention comprise the distal portion which is inserted into the body and which applies the therapy to the required location, the proximal portion of the device may suitably comprise the user interface and energy connection functions. The proximal end of the device of the invention is located outside of the patient's body when in use and provides a user interface, typically in the form of a handle grip or hub 50 as well as a means for connecting the guidewire 10 to an energy source. The energy connection may be in the form of a direct connection to an energy source, such as an RF generator. In this arrangement the application of energy to the electrode(s) at the distal tip is achieved by activating the energy source.

Figure 10:
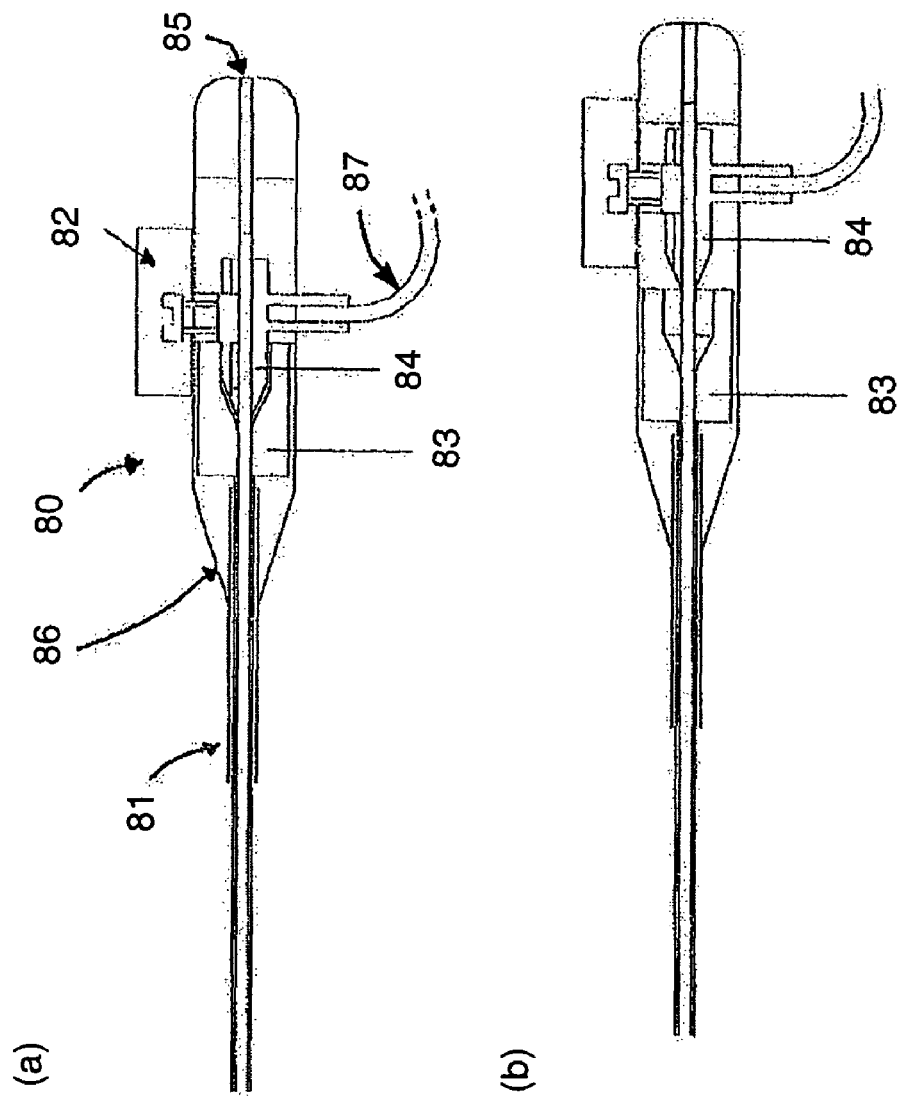
FIG. 10 shows a cut away side view of the proximal end of an embodiment of the device of the invention which provides the user interface in the form of a handle grip, (a) shows the configuration of the grip in which the plug and socket means are engaged to allow electrical connection. (b) shows the configuration of the grip in which the plug and socket means are separated so that no electrical connection is made.

Alternatively, an embodiment of the invention is shown in FIGS. 10 (a) and (b) which shows a hub 80 comprising a plug and socket arrangement 83,84 that can be slidably mounted over a guidewire which passes through central channel 85 defined by the housing 86 and a barrel 81. The plug 86 is connected to an RF source via a lead 87, and can engage the socket 83 through the action of the user pushing the attached slider 82 in a distal (i.e. forward) direction. The guidewire is in electrical contact with the socket 83 and thus when the plug 84 and socket 83 are engaged the RF source can be activated to apply RF energy at the therapy site via the guidewire or the electrode(s) located at the distal tip of the guidewire. The arrangement also allows for ease of connection to the remote energy source after the guidewire 10 has been positioned correctly.

Figure 11:
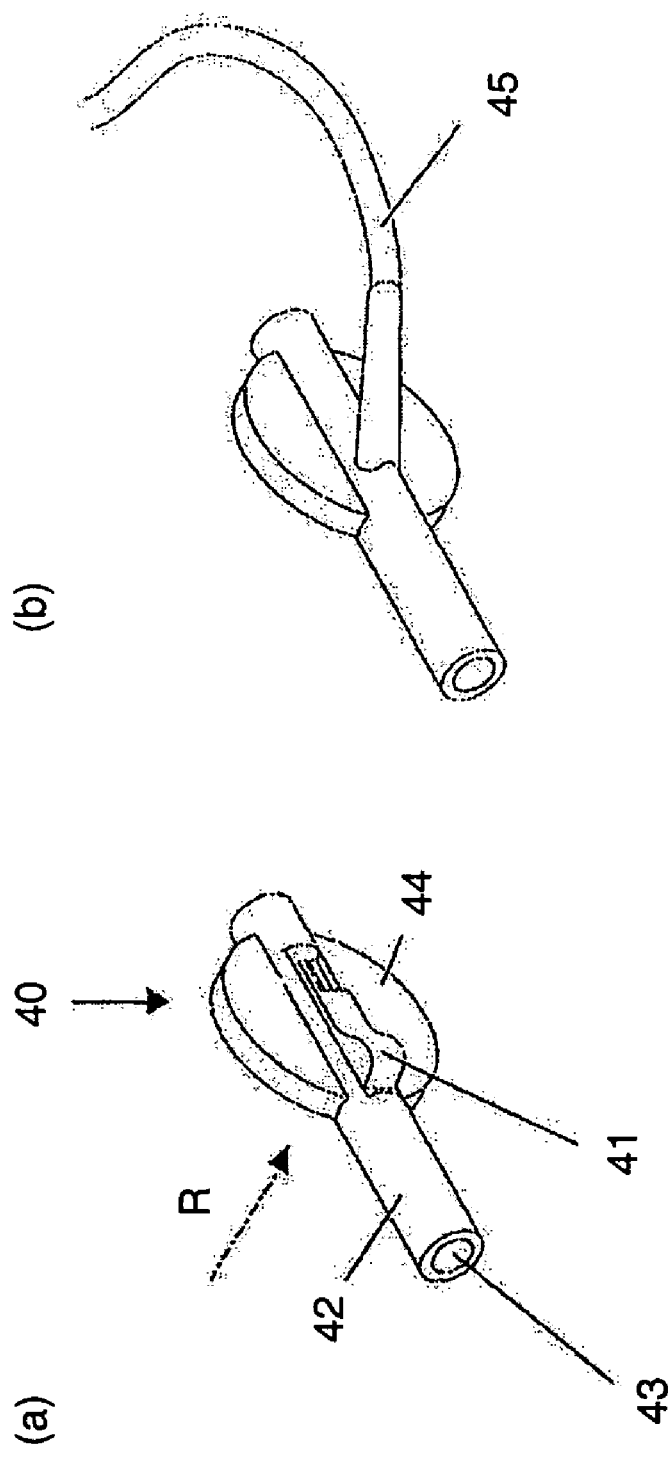
FIG. 11 shows an alternative embodiment of the invention which provides the user interface and electrical connector in the form of a slidably removable housing. (a) shows a perspective view of the housing with the slidable switch apparent, (b) shows the reverse view along line R of FIG. 8 (a) where the entry point of the electrical cable into the housing is apparent.
Figure 12:
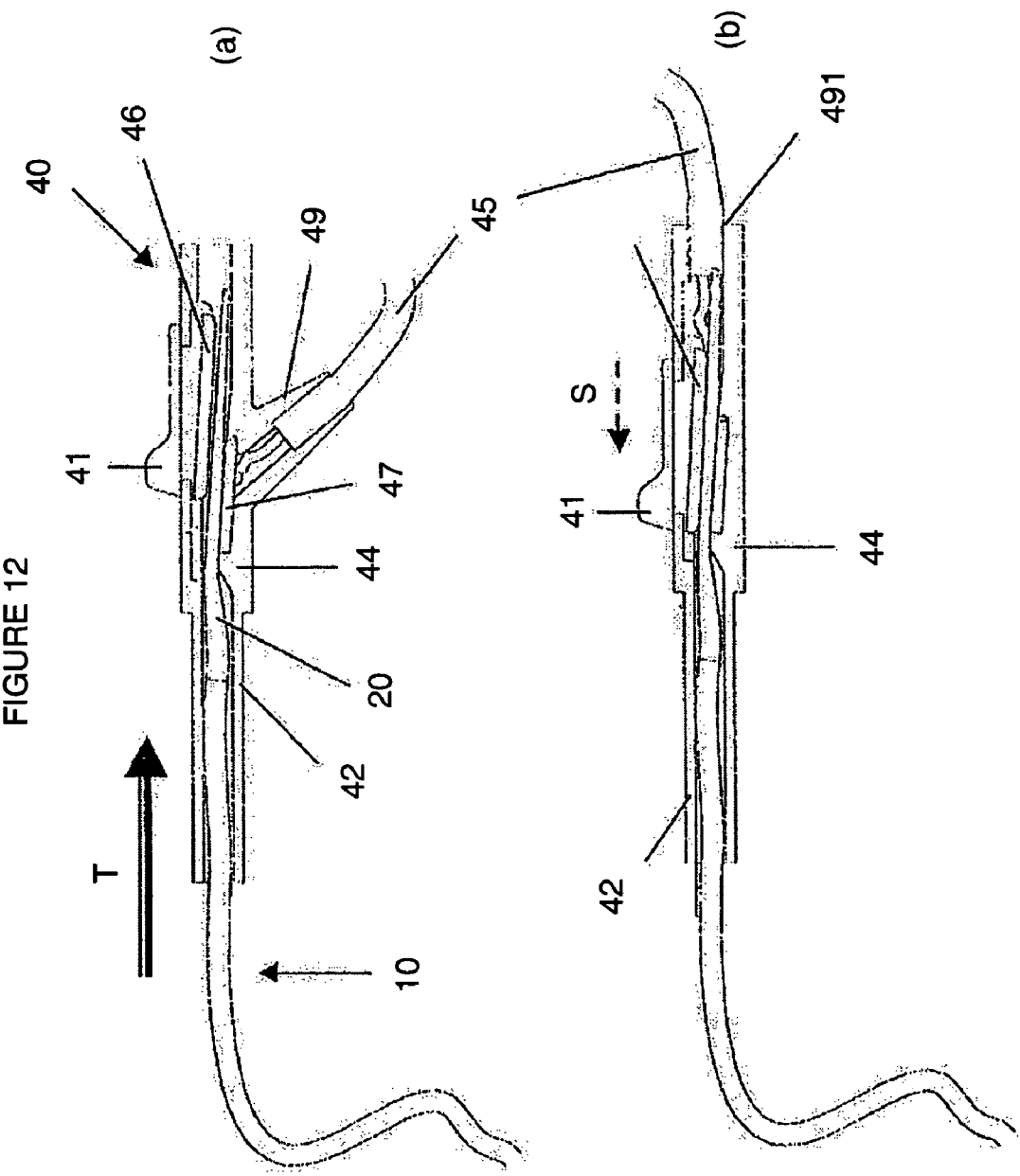
FIG. 12 shows a top-down cut away view of the user interface shown in FIG. 11 (a) shows an embodiment wherein the electrical cable enters the housing via a side port (as in FIG. 11 (a)), (b) shows an alternative embodiment wherein the electrical cable enters via a port located in the rearward face of the housing.

In a specific embodiment of the invention shown in FIGS. 11 and 12, a slidably mounted electrical interface hub 40 is provided. The hub 40 comprises a body 44 upon which is located a sliding actuator or switch 41, and a barrel 42 which defines a bore 43 (see FIG. 11 (a)). The barrel 42 extends though the central portion of the body 44 and allows for slidable mounting of the hub 40 on a guidewire 10 which passes though the bore 43. A lead 45 to the RF energy source is connected to the body 44 (see FIG. 11 (b)).

In FIG. 12 (a) the internal features of a first embodiment of the invention are shown. The guidewire 10 is inserted into the hub 40 via the barrel 42 along the direction shown by arrow T. A portion of the central core 20 of the guidewire 10 is exposed at the proximal end so as to permit electrical connection between the central conducting core 22 and the external energy source. Within the body 44 of the hub 40 the exposed portion of the central core 20 is located between a contact pad 47 and an angled foot 46. The contact pad 47 is in electrical contact with the remote energy source via the lead 45 which enters the hub via port 49. The foot 46 is attached to the sliding actuator 41, which is slidable along the longitudinal axis of the guidewire 10 from a released position to a locking position, as shown by arrow S (see FIG. 12 (b)). In the released position the foot 46 does not contact the central core 20 and there is free movement of the guidewire 10 within the hub 40. When the sliding actuator is moved to the locking position the angled foot 46 is brought to bear upon the central core 20 thereby urging it into contact with the contact pad 47, establishing an electrical contact between the central conducting core 22 of the guidewire 10 and the remote energy source. An alternative arrangement is shown in FIG. 12 (b) in which the lead 45 enters the hub via a proximally directed port 491. In this embodiment of the invention the contact pad 47 does not serve as the source of the electrical connection but cooperates with the angled foot 46 to lock the guidewire 10 into position such that electrical connection with contacts at the terminus of the lead 45 can be established.

Figure 13:
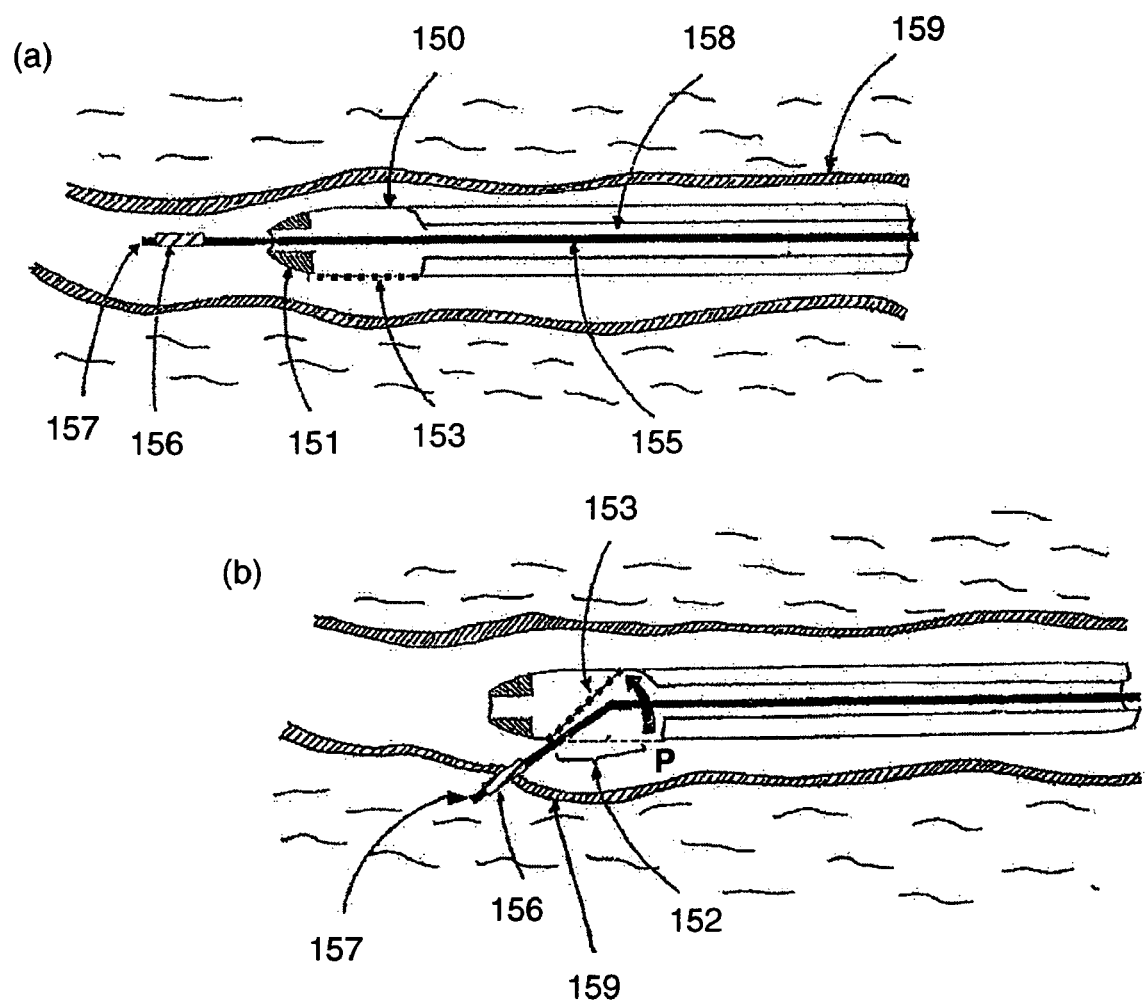
FIG. 13 shows a diagrammatic side view of an embodiment of the invention in which (a) a catheter is loaded onto the guidewire of the invention and is tracked to the site requiring therapy within the patient's body. (b) the catheter comprises a side port with a hinged gate that can open inwardly, along arrow P, into the central lumen of the catheter when the guidewire is withdrawn proximally, and act as a deflector to direct the reinserted guidewire outwardly so that it will penetrate the wall of the surrounding hollow anatomical structure.

In an embodiment of the invention the device is able to cooperate with a catheter loaded thereupon either via a monorail or over-the-wire mounting. In this configuration, the catheter comprises a elongate body including a lumen, through which the guidewire device of the invention is located. As shown in FIG. 13, a catheter 150 is slidably mounted over a guidewire 155. Optionally, the catheter 150 may comprise an RF electrode 151 located at the distal tip. An aperture 152 is positioned in the side wall of the catheter proximally to the distal end of the catheter. The aperture is sealed via a pivotally mounted door 153. In use, the catheter 150 is slidably mounted onto the prepositioned guidewire 155 and located to the position in the body where therapy is required. The guidewire 155 is then withdrawn proximally until the distal tip of the guidewire 157 is withdrawn into the central lumen 158 of the catheter 150 to a point that is proximal relative to the location of the aperture 152. Optionally the guidewire 155 can be withdrawn completely and substituted with a therapeutic guidewire according to the present invention and substantially as described in any of the preceding embodiments. Retraction of the guidewire proximally causes the door 153 to open inwardly (along arrow P in FIG. 13(*b*)) via a user induced release mechanism (not shown) or simply by biasing the door 153 to spring open when the guidewire 155 is withdrawn. The guidewire 155 is then advanced proximally and is deflected out of the body of the catheter 150 through the aperture 152 and into the wall 159 of the surrounding hollow anatomical structure. In the bipolar configuration the RF electrode 156 on the guidewire 155 can cooperate with the RF electrode 151 on the catheter. In an alternative embodiment of the invention, the catheter 150 does not comprise an electrode 151 and so the guidewire operates in a monopolar configuration.

Optionally, the guidewire 155 can be configured to adopt a helical conformation once it has exited the aperture 152. This can be achieved by manufacturing at least the distal portion of the guidewire 155 from a shape memory alloy, for example. Hence, once the distal tip of the guidewire 155 has exited the aperture 152 it is able to spiral about the longitudinal axis of the catheter body in a distal direction through the tissue surrounding the hollow anatomical structure. In this embodiment, it is possible to configure the guidewire 155 to exert additional contraction force upon the hollow structure during the thermal phase by configuring the initial diameter of the helix prior to thermal ablation such that it is greater than the diameter assumed following transition. In a specific embodiment of the invention, suitably but not exclusively adapted to an endoscopic procedure for fallopian tubal ligation, the distal tip of the guidewire 155 is preformed from a shape memory alloy such that on emergence from the aperture 152 in the side wall of the catheter 150 it penetrates through the wall of the fallopian tube, into the underlying muscular or serous tissue, and coils around the perimeter of the tube. On heating above the austenitic finish temperature (Af) the guidewire 155 reverts to the austenitic state which is arranged to be in the form of tighter helical coil (as described above) thereby facilitating occlusion of the tube. Optionally, the distal tip of the guidewire 155 may be detached and allowed to remain in situ by utilising one of the detachment mechanisms described in previous embodiments of the present invention (see above).

The guidewire devices of the invention can suitably by manufactured from materials that include stainless steel, platinum, gold, silver, titanium, a metal alloy or, when required, a shape memory alloy such as nitinol.

Although particular embodiments of the invention have been disclosed herein in detail, this has been done by way of example and for the purposes of illustration only. The aforementioned embodiments can be utilised alone or in combination and are not intended to be limiting with respect to the scope of the appended claims, which follow. It is contemplated by the inventors that various substitutions, alterations, and modifications may be made to the invention without departing from the spirit and scope of the invention as defined by the claims.

The invention claimed is:

1. A device suitable for insertion into a hollow anatomical structure within a patient via a percutaneous, laparoscopic or endoscopic route for the purpose of ablating tissue within or surrounding the hollow structure so as to induce occlusion of the hollow structure, the device comprising:
   a guidewire having a distal end and a proximal end, the guidewire comprising a central core which extends along the length of the body, the central core comprising at least one conductor and a plurality of steering members, a tip located at the distal end of the guidewire wherein the tip comprises at least one heating module and means for connecting the at least one conductor to an external energy source, said means being located at the proximal end of the guidewire;
   a catheter having a elongate body including a lumen extending along at least a portion of the elongate body, wherein the lumen is adapted to facilitate slidable mounting of the catheter on the guidewire, an aperture positioned in the side wall of the catheter proximally to the distal end of the catheter, the aperture being sealable via a pivotally mounted door; and
   wherein, in use, the guidewire can be withdrawn proximally until the distal tip of the guidewire is located within the lumen of the catheter at a point that is adjacent to the aperture which permits the door to be opened inwardly, such that upon subsequent advancement of the guidewire the tip is deflected outwardly from the lumen of the catheter through the aperture and into the surrounding hollow anatomical structure where the at least one heating module can be activated so as to induce ablation of the tissue.

2. The device of claim 1, wherein the device comprises a mechanism for permitting in situ detachment of the distal tip following activation of the at least one heating module.

3. The device of claim 1 wherein the hollow structure is selected from the group consisting of: a vein; an artery; an arteriole; a fallopian tube; a biliary duct; a ureter; a urethra; a bronchiole; and a vas deferens.

* * * * *